(12) United States Patent
Janssen et al.

(10) Patent No.: US 6,320,048 B1
(45) Date of Patent: Nov. 20, 2001

(54) 3-PIPERIDINYL-1,2-BENZISOXAZOLES

(75) Inventors: Cornelus Gerardus Maria Janssen, Vosselaar; Alfonsus Guilielmus Knaeps, Herentals; Ludo Edmond Josephine Kennis, Turnhout; Jan Vandenberk, Beerse, all of (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 08/100,907

(22) Filed: Aug. 3, 1993

Related U.S. Application Data

(62) Division of application No. 07/932,142, filed on Aug. 8, 1992, now Pat. No. 5,254,556, which is a division of application No. 07/422,847, filed on Oct. 17, 1989, now Pat. No. 5,158,952, which is a continuation-in-part of application No. 07/267,857, filed on Nov. 7, 1988, now abandoned.

(51) Int. Cl.$^7$ .......................... C07B 57/00; C07D 487/04
(52) U.S. Cl. ............................................. 544/282
(58) Field of Search ................................ 544/282

(56) References Cited

U.S. PATENT DOCUMENTS

| | | | |
|---|---|---|---|
| 3,687,958 | * 8/1972 | Plostnieks | 260/293.72 |
| 3,907,813 | * 9/1975 | Jansson | 260/293.79 |
| 4,054,570 | * 10/1977 | Huebner | 424/263 |
| 4,571,424 | * 2/1986 | Christensen | 546/276 |
| 4,879,300 | * 11/1989 | Giordani | 546/237 |
| 5,220,016 | * 6/1993 | Magnus | 540/478 |

OTHER PUBLICATIONS

Cornelus Janssen, J. Labelled Compounds and Radiopharm. 24, 909 (1987).*

* cited by examiner

*Primary Examiner*—Mark L. Berch

(57) ABSTRACT

There is disclosed a process for preparing an enantiomeric form of the compound having the formula:

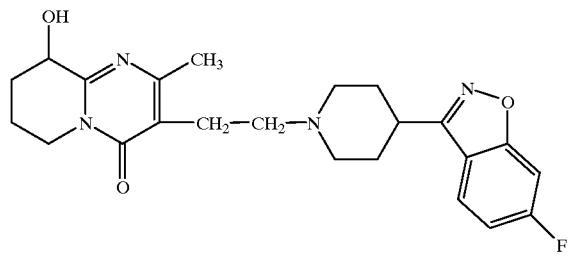

or a pharmaceutically acceptable acid addition salt thereof, wherein said process comprises the steps of:

(a) reacting a racemic mixture of said compound with a chiral acid or acid chloride selected from the group consisting of tartaric acid, malic acid, mandelic acid, camphor sulfonic acid, 4,5-dihydro-1H-2-benzopyran-2-carboxylic acid, and the acid chlorides thereof, to form a mixture of diastereomeric salts or esters;

(b) physically separating said mixture of diastereomeric salts or esters by selective crystallization or chromatography; and (c) converting said separated diastereomeric salts or esters into the corresponding enantiomeric forms of said compound by hydrolysis in an acidic or basic aqueous medium.

6 Claims, No Drawings

3-PIPERIDINYL-1,2-BENZISOXAZOLES

CROSS-REFERENCE TO RELATED APPLICATION

This application is a division of our application Ser. No. 07/932,142, filed Aug. 8, 1992, now U.S. Pat. No. 5,254, 556, which in turn was a division of application Ser. No. 07/422,847, filed Oct. 17, 1989, now U.S. Pat. No. 5,158, 952, which in turn was a continuation-in-part of application Ser. No. 07/267,857, filed Nov. 7, 1988, now abandoned.

BACKGROUND OF THE INVENTION

In EP-A-0,196,132 there are described a number of 3-piperidinyl-1,2-benz-isoxazoles having antipsychotic activity.

The compounds of the present invention differ therefrom by the specific substitution on the (2-$C_{1-4}$alkyl-6,7,8,9-tetrahydro-4-oxo-4$\underline{H}$-pyrido[1,2-a]-pyrimidin-3-yl)alkyl substituent at the 1 position of the piperidinyl moiety.

DESCRIPTION OF THE INVENTION

The present invention is concerned with novel 3-piperidinyl-1,2-benzisoxazoles having the formula

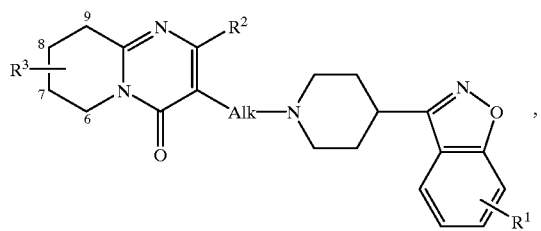

(I)

the pharmaceutically acceptable acid addition salts thereof, and the stereochemically isomeric forms thereof, wherein Alk is $C_{1-4}$alkanediyl;

$R^1$ is hydrogen, $C_{1-4}$alkyl or halo;

$R^2$ is $C_{1-4}$alkyl;

$R^3$ is hydroxy or $R^4$—C(=O)O—; and $R^4$ is $C_{1-19}$alkyl.

In the foregoing definitions $C_{1-4}$alkanediyl defines bivalent straight and branch chained alkanediyl radicals having from 1 to 4 carbon atoms such as, for example, methylene, 1,2-ethanediyl, 1,3-propanediyl, 1,4-butanediyl and the branched isomers thereof; $C_{1-4}$alkyl defines straight and branch chained saturated hydrocarbon radicals having from 1 to 4 carbon atoms such as, for example, methyl, ethyl, propyl, 1-methylethyl, butyl, 1-methylpropyl, 2-methylpropyl and 1,1-dimethyl-ethyl; $C_{1-19}$alkyl defines $C_{1-4}$alkyl radicals as defined hereinabove and the higher homologs thereof having from 5 to 19 carbon atoms such as, for example, pentyl, hexyl, heptyl, octyl, nonyl, decyl, undecyl, dodecyl, tridecyl, tetradecyl, pentadecyl, hexadecyl, heptadecyl, octadecyl, nonadecyl and the like; halo is generic to fluoro, chloro, bromo and iodo. $R^3$ as defined hereinabove may be substituted on any of the 6,7,8 or 9 positions of the 6,7,8,9-tetrahydro-2-$C_{1-4}$alkyl-4$\underline{H}$-pyrido[1,2-a]pyrimidin-4-one moiety.

Particular compounds are those compounds of formula (I) wherein $R^3$ is substituted on the 9 position of the 6,7,8,9-tetrahydro-2-$C_{1-4}$alkyl-4$\underline{H}$-pyrido[1,2-a]pyrimidin-4-one moiety.

More particular compounds within the invention are those particular compounds wherein Alk is ethanediyl; and/or $R^1$ is halo, in particular fluoro and more in particular 6-fluoro; and/or $R^2$ is methyl.

Among the above defined groups of compounds of formula (I) those compounds wherein $R^4$ is $C_{7-13}$alkyl, in particular heptyl, nonyl, undecyl or tridecyl are of particular interest.

The most interesting compounds within the invention are selected from the group consisting of 3-[2-[4-(6-fluoro-1,2-benzisoxazol-3-yl)-1-piperidinyl]ethyl]-6,7,8,9-tetrahydro-9-hydroxy-2-methyl-4$\underline{H}$-pyrido[1,2-a]pyrimidin-4-one, the pharmaceutically acceptable acid addition salt forms and the enantiomeric forms thereof.

From formula (I) it is evident that the compounds of this invention have at least one asymmetric carbon atom in their structure, namely the carbon atom bearing the $R^3$ substituent. The absolute configuration of this centre may be indicated by the stereo-chemical descriptors R and S, this R and S notation corresponding to the rules described in Pure Appl. Chem. 1976, 45, 11–30. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of the invention.

The compounds of formula (I) can generally be prepared by $\underline{N}$-alkylating a 3-piperidinyl-1,2-benzisoxazole of formula (II) with an alkylating reagent of formula (III) following art-known $\underline{N}$-alkylation procedures.

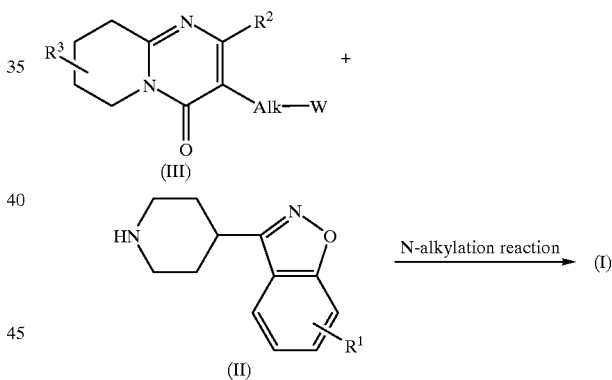

In formula (III) W represents an appropriate reactive leaving group such as, for example, halo, e.g. chloro, bromo or iodo; sulfonyloxy, e.g. methanesulfonyloxy, trifluoromethanesulfonyloxy, benzenesulfonyloxy, 4-methylbenzenesulfonyloxy and the like leaving groups. Said $\underline{N}$-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxy-benzene and the like; a $C_{1-6}$alkanol, e.g. methanol, ethanol, 1-butanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. $\underline{N},\underline{N}$-dimethylformamide, $\underline{N},\underline{N}$-dimethylcetamide, dimethylsulfoxide, pyridine, 1,3-dimethyl-3,4,5,6-tetrahydro-2(1$\underline{H}$)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation under an inert atmosphere such as, for example, oxygen-free argon or nitrogen gas.

Alternatively, said N-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the medium and, if necessary, further purified according to methodologies generally known in the art such as, for example, extraction, crystallization, trituration and chromatography.

The compounds of formula (I) can also be obtained by the cyclization of an oxime of formula (IV), wherein Y is a reactive leaving group such as, for example, halo or nitro. Preferably Y is a halo group and more particularly fluoro.

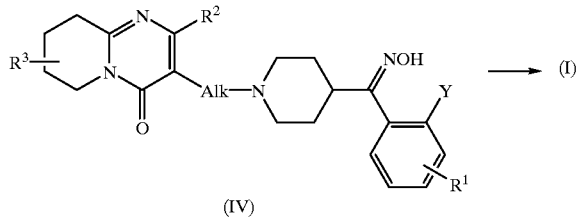

Said cyclization reaction of the oxime of formula (IV) may conveniently be conducted by treatment with an appropriate base, preferably in a suitable reaction-inert solvent at temperatures in the range of 20° to 200° C., preferably at 50° to 150° C., and in particular at the reflux temperature of the reaction mixture. Or, if desirable, said base may first be added, preferably at room temperature, whereupon the thus formed oxime salt is cyclized, preferably at an increased temperature and more preferably at the reflux temperature of the reaction mixture. Appropriate bases for said cyclization are, for example, alkali and earth alkaiine metal carbonates, hydrogen carbonates, hydroxides, alkoxides or hydrides, e.g. sodium carbonate, sodium hydrogen carbonate, potassium carbonate, sodium hydroxide, sodium methoxide, sodium hydride or organic bases such as amines, e.g. N,N-diethylethanamine, 4-ethylmorpholine and the like bases. Suitable solvents are, for example, water; aromatic hydrocarbons, e.g. benzene, methylbenzene, dimethylbenzene and the like; halogenated hydrocarbons, e.g. dichloromethane, trichloromethane, 1,2-dichloroethane and the like; lower alkanols, e.g. methanol, ethanol, 1-butanol and the like; ketones, e.g. 2-propanone, 4-methyl-2-pentanone and the like; ethers, e.g. 1,4-dioxane, tetrahydrofuran and the like; dipolar aprotic solvents, e.g. N,N-dimethylformamide, N,N-dimethylacetamide, dimethylsulfoxide, 1-methyl-2-pyrrolidinone and the like, or mixtures of such solvents.

The compounds of formula (I) can also be obtained by cyclizing an activated oxime derivative of formula

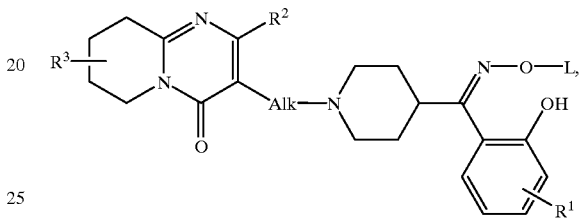

wherein L is an acid residue and more particularly is formyl, ($C_{1-6}$alkyl or aryl)carbonyl, e.g. acetyl, propionyl, benzoyl and the like; ($C_{1-6}$alkyl or aryl)oxycarbonyl, e.g. methoxycarbonyl, ethoxycarbonyl, (1,1-dimethyl)ethoxycarbonyl, phenyloxycarbonyl and the like; ($C_{1-6}$alkyl or aryl)sulfonyl, e.g. methanesulfonyl, benzenesulfonyl, 4-methylbenzenesulfonyl, 2-naphthalenesulfonyl and the like; N-acylaminocarbonyl, e.g. trichloromethylcarbonylaminocarbonyl and the like. Said cyclization reaction of the activated oxime derivative of formula (V) may conveniently be conducted by treatment with an appropriate base, preferably in a suitable reaction-inert solvent, at temperatures in the range from 20° to 200° C., particularly from 50° to 150° C. and preferably at the reflux temperature of the reaction mixture. In some instances however, it may be advantageous not to add a base to the reaction mixture and to remove the acid liberated during the reaction by destination at normal pressure or, if desired, at reduced pressure. Alternatively, said cyclization may also be effected by heating the oxime derivative (V) in vacuo without a solvent. Appropriate bases are for example, alkali and earth alkaline metal carbonates, hydrogen carbonates and organic amines, e.g. sodium carbonate, potassium carbonate, sodium hydrogen carbonate, N,N-diethylethanamine, 4-ethylmorpholine, 1,4-diazabicyclo[2.2.2]octane, pyridine and the like bases. Suitable solvents for said cyclization are, for example, aromatic hydrocarbons, e.g. benzene, methylbenzene, dimethylbenzene and the like; ethers, e.g. 1,1'-oxybisethane, 1,1'-oxybisbutane, tetrahydrofuran, 1,4-dioxane, 1,1'-oxybis[2-methoxyethane], 2,5,8,11-tetraoxadodecane and the like; dipolar aprotic solvents, e.g. N,N-dimethylformamide, N,N-dimethylacetamide, 1-methyl-2-pyrrolidinone, hexamethylphosphoric triamide, pyridine, acetic anhydride and the like; halogenated hydrocarbons, e.g. trichloromethane, tetrachloromethane, 1,2-dichloroethane, chlorobenzene and the like solvents.

The compounds of formula (I) wherein $R^3$ is $R^4$—(C═O)—O—, said compounds being represented by formula (I-b), can be obtained by the O-acylation reaction of a compound of formula (I-a) wherein $R^3$ is hydroxy, with a carboxylic acid of formula (VI) or a suitable reactive functional derivative thereof such as, for example, an acyl halide, symmetric or mixed anhydride, ester or amide, acyl azide and the like derivatives. Said functional derivatives may be prepared following art-known methods, for example, by reacting the carboxylic acid of formula (VI) with a halogenating reagent such as, for example, thionyl chloride, phosphorous trichloride, phosphoryl chloride, oxalyl chloride and the like, or by reacting said carboxylic acid (VI) with an acyl halide such as acetyl chloride and the like. Said derivatives may be generated in situ, or if desired, be isolated and further purified before reacting them with the compound of formula (I-a).

N,N-dimethylformamide, N,N-dimethylacetamide, or pyridine and the like. In some instances it may be appropriate to employ an excess of one of the reagents as solvent. The water, acid, alcohol or amine which is liberated during the course of the reaction may be removed from the reaction mixture by art-known procedures such as, for example, azeotropical distillation, complexation, salt formation and the like methods. In some instances particularly the addition of a suitable base such as, for example, a tertiary amine, e.g. N,N-diethyl-ethanamine, 4-ethylmorpholine, pyridine or N,N-dimethyl-4-aminopyridine, may be appropriate. Further, in order to enhance the rate of the reaction, said acylation reaction may advantageously be conducted at a

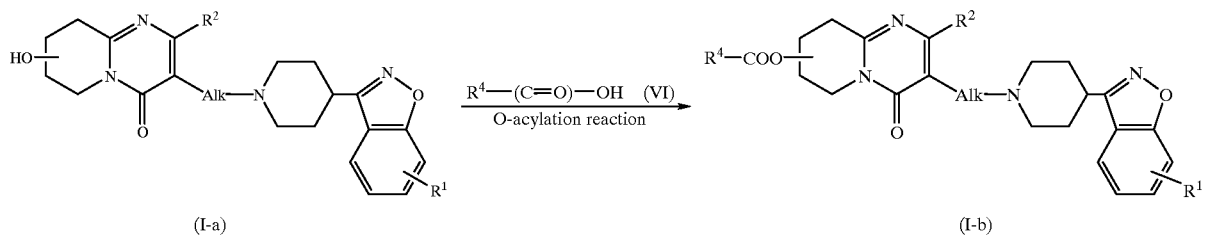

(I-a)  (I-b)

Alternatively, the compound of formula (I-a) and the carboxylic acid of formula (VI) may also be esterified in the presence of a suitable reagent capable of forming esters such as, for example, a dehydrating reagent, e.g. dicyclohexylcarbodiimide, 2-chloro-1-methylpyridinium iodide, phosphorus pentoxide, 1,1'-carbonylbis[1H-imidazole], 1,1'-sulfonyl bis[1H-imidazole] and the like reagents.

Said O-acylation reactions can conveniently be carried out by stirring the reactants optionally in a suitable reaction-inert solvent such as, for example, a halogenated hydrocarbon, e.g. dichloromethane, trichloromethane and the like; an aromatic hydrocarbon, e.g. benzene, methylbenzene and the like; an ether, e.g. 1,1'-oxybisethane, tetrahydrofuran and the like; or a dipolar aprotic solvent, e.g.

somewhat elevated temperature, and in particular instances at the reflux temperature of the reaction mixture.

The compounds of formula (I) can also be prepared following art-known cyclization procedures for preparing pyrimidin-4-ones such as, for example, by reacting an amidine of formula (VII) with a β-dicarbonyl intermediate of formula (VIII), or by cyclizing a reagent of formula (IX) with an enamine of formula (X). In formulae (VIII), (IX) and (X) $R^5$ represents an appropriate leaving group such as, for example, $C_{1-6}$alkyloxy, hydroxy, halo, amino, mono- or di-($C_{1-6}$alkyl)amino and the like.

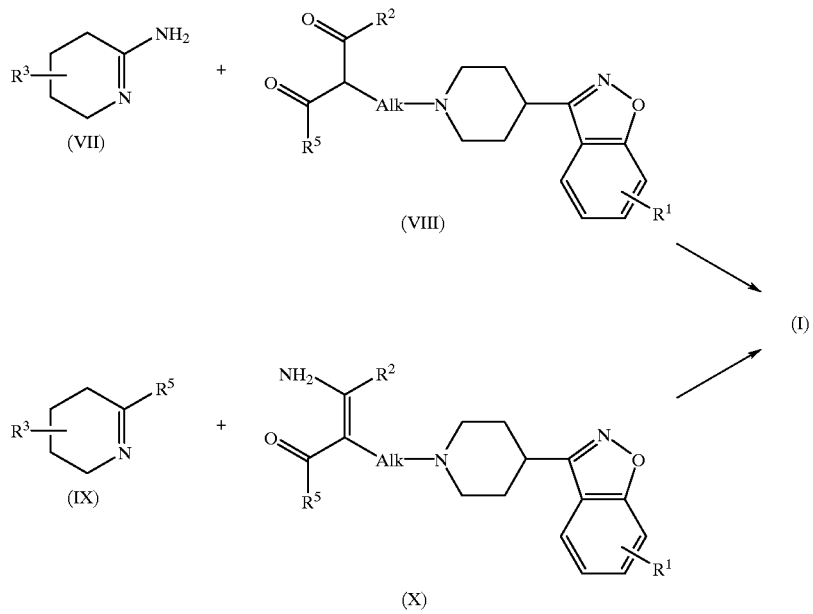

Said cyclization reactions may generally be carried out by stirring the reactants, optionally in the presence of a suitable reaction-inert solvent such as, for example, an aliphatic, alicyclic or aromatic hydrocarbon, e.g. hexane, cyclohexane, benzene and the like; pyridine, N,N-dimethylformamide and the like dipolar aprotic solvents. In order to enhance the rate of the reaction it may be appropriate to increase the temperature, more particularly, it may be recommendable to carry out the reaction at the reflux temperature of the reaction mixture.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic acid and the like, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted into the free base form by treatment with alkali.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

Enantiomeric forms of the compounds of formula (I-a)

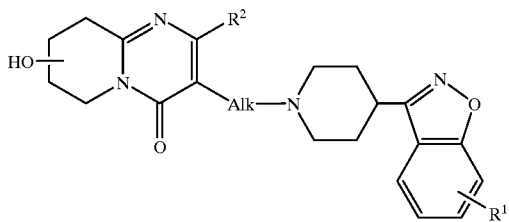

(I-a)

can be obtained by converting the racemic mixtures of the compounds of formula (I-a) with a suitable resolving reagent such as, for example, a chiral acid, e.g. tartaric, malic and mandelic acids, campher sulfonic acid, 4,5-dihydro-1 H-2-benzopyran-2-carboxylic acid and the like, or the reactive functional derivatives thereof, e.g. the acyl halides, to a mixture of diastereomeric salts or compounds, particularly esters; physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomeric forms of the compounds of formula (I-a) by hydrolysis in an acidic or basic aqueous medium, optionally at an elevated temperature.

Some of the intermediates and starting materials for use in the foregoing preparations are known compounds, while others are novel. The intermediates of formula (II) and methods of preparing them are known from EP-A-0,196, 132. The alkylating reagents of formula (III) are novel and can be prepared according to artknown methodologies of preparing similar compounds and will be described hereinafter in more detail.

By condensing an optionally protected 2-aminopyridine derivative (XI) with an α-acyl lactone (XII) in the presence of an activating reagent in a suitable reaction-inert solvent, an intermediate of formula (XIII) can be obtained.

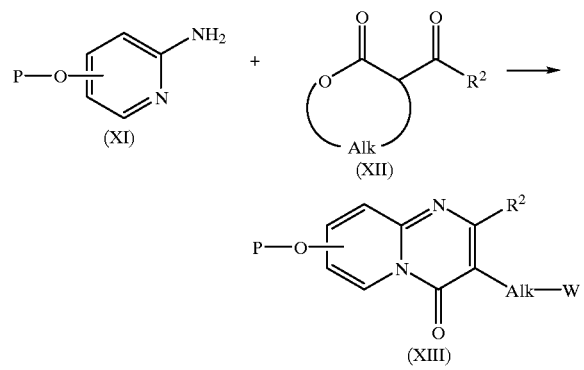

In the formulae (XI), (XIII) and hereinafter whenever it occurs, P represents hydrogen or a protective group which can be readily removed such as, for example, a hydrogenolyzable group, e.g. phenylmethyl and the like; a hydrolyzable group, e.g. methyl and the like. Appropriate activating reagents for said condensation reaction typically are halogenating reagents such as, for example, phosphoryl chloride, phosphoryl bromide, phosphorous trichloride, thionyl chloride and the like reagents.

The subsequent catalytic hydrogenation of intermediate (XIII) in a suitable reaction-inert solvent in the presence of hydrogen, optionally at an elevated temperature and/or pressure, with a catalyst such as, for example, palladium-on-charcoal and the like, can yield a protected intermediate (XIV) in case P is an alkyl group such as, for example, methyl;

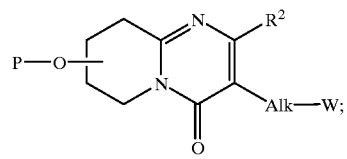

(XIV)

or, on the other hand, when P is hydrogen or a hydrogenolyzable group such as, for example, phenylmethyl, an alkylating reagent of formula (III-a) wherein $R^3$ is hydroxy can be obtained directly.

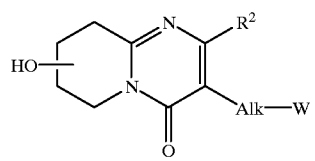

(III-a)

Suitable solvents for said catalytic hydrogenation reaction comprise water, $C_{1-4}$alkanols, e.g. methanol, ethanol, 2-propanol and the like; ethers, e.g. 1,1'-oxybisethane, 1,4-dioxane, tetrahydrofuran, 2-methoxyethanol and the like; halogenated hydrocarbons, e.g. trichloromethane and the like; dipolar aprotic solvents, e.g. N,N-dimethylformamide and the like; esters, e.g. ethyl acetate, butyl acetate and the like; or a mixture of such solvents.

The intermediate (XIV) wherein P represents an alkyl group may be deprotected to a reagent of formula (III-a) by heating the former with concentrated hydrobromic or hydroiodic acid or by reaction with Lewis acids such as, for example, boron trihalides, e.g. boron trifluoride, boron trichloride and in particular boron tribromide; iodotrimethylsilane; or aluminum chloride and the like Lewis acids.

The intermediate of formula (III-a) may be O-acylated with a carboxylic acid of formula (VI) or a functional derivative thereof as defined hereinabove, to an alkylating reagent of formula (III-b) wherein $R^3$ is $R^4$—C(=O)—O— following the same procedures as described hereinabove for the O-acylation of the compounds of formula (I-a).

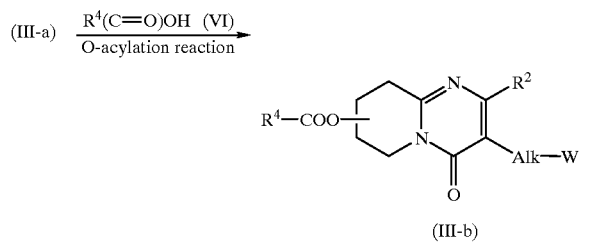

The intermediates of formula (IV) may be prepared by N-alkylating a reagent of formula (III) with an oxime derivative of formula (XV) following the same procedures as described hereinabove for the preparation of the compounds of formula (I) from the intermediates (II) and (III). The derivatives (XV) are known from EP-A-0,196,132.

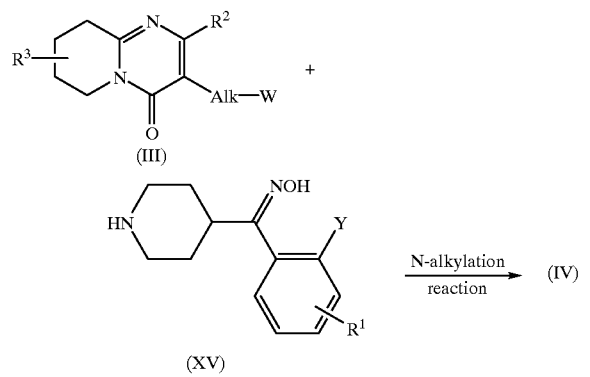

The intermediates of formula (V) may be obtained by reacting an oxime of formula (XVI) with an activated acid derivative of formula L-$W^1$ (XVII),

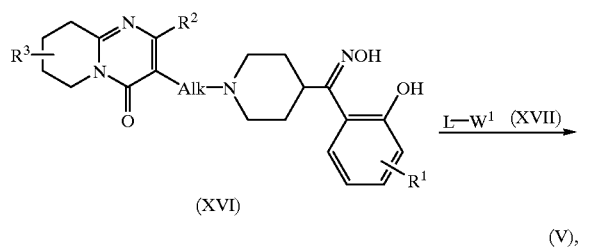

wherein L is an acid residue as defined hereinabove and $W^1$ represents a reactive leaving group such as, for example, halo, (aryl or $C_{1-6}$alkyl)carbonyloxy, (aryl or $C_{1-6}$alkyl)oxy and the like. As typical examples of the reagent of formula (XVII) there may be mentioned carboxylic acid anhydrides, e.g. acetic anhydride, benzoic anhydride and the like; carboxylic acid halides, e.g. acetyl chloride, benzoyl chloride and the like; carbono-chloridates, e.g. methyl, ethyl or phenyl carbonochloridate and the like; di($C_{1-6}$alkyl) carbonates, e.g. dimethylcarbonate, diethylcarbonate and the like. The reaction of the intermediates (XVI) with the activated acid derivatives (XVII) may be carried out following art-known esterification procedures, e.g. by stirring the reactants at a somewhat elevated temperature, preferably in a reaction-inert solvent such as, for example, an aromatic hydrocarbon, e.g. benzene, methylbenzene and the like; a halogenated hydrocarbon, e.g. dichloromethane, trichloromethane and the like; a ketone, e.g. 2-propanone, 4-methyl-2-pentanone and the like; an ether, e.g. 1,1'-oxybisethane, 1,4-dioxane and the like; a dipolar aprotic solvent, e.g. N,N-dimethylformamide, pyridine and the like solvents. In some instances it may be appropriate to add a suitable base such as, for example, N,N-diethylethanamine, N-(1-methylethyl)-2-propanamine, 4-ethylmorpholine, N,N-dimethyl-4-aminopyridine and the like bases to the reaction mixture.

The intermediate of formula (XVI) in turn may be prepared by N-alkylating a reagent of formula (III) with an oxime derivative of formula (XVIII)

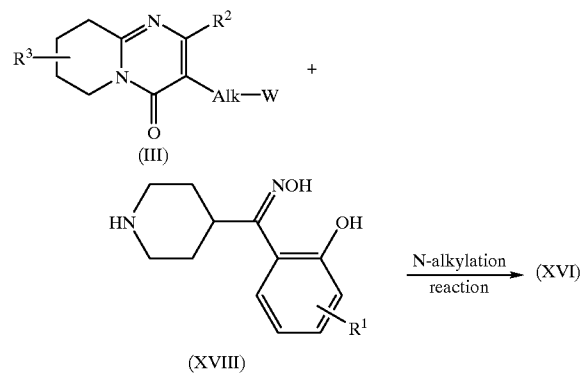

following the same procedures as described hereinabove for the preparation of the compounds of formula (I) from the intermediates (II) and (III).

The compounds of formula (I) and some of the intermediates in the present invention contain at least one asymmetric carbon atom. Pure stereochemically isomeric forms of said compounds and said intermediates can be obtained by the application of artknown procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the pharmaceutically acceptable acid addition salts and stereochemically isomeric forms thereof, are potent antagonists of neurotransmitters and in particular of the mediators serotonin and dopamine. Antagonizing said mediators will suppress or relieve a variety of symptoms associated with phenomena induced by the release, in particular the excessive release, of these mediators. Therapeutic indications for using the present compounds are mainly in the CNS area, the gastrointestinal and cardiovascular field and related domains. The compounds of formula (I) are particularly useful as antipsychotic agents. Serotonin antagonists are reportedly effective in combatting psychoses, aggressive behaviour, anxiety, depression and migraine. Dopamine receptor antagonists are known to have neuroleptic properties. Combined serotonin-dopamine antagonists are especially interesting as they appear to offer relief of both the positive and negative symptoms of schizophrenia. Further the present compounds also appear to be useful therapeutic agents for combatting autism. Therapeutic applications in the gastrointestinal field comprise their use as, for instance, anti-diarrhoeals, inhibitors of gastro-oesophageal reflux and particularly antiemetics, e.g. in cancer patients receiving chemotherapy and radiation treatment. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits.

The compounds of formula (I) show the additional advantage of being eliminated rather slowly from the body and thus of being long acting. This can be evidenced, for example, by measuring the plasma levels after oral administration to dogs and by the long acting antiemetic effect exerted by the present compounds on dogs challenged with the dopamine agonist apomorphine. Especially the compounds of formula (I) wherein $R^3$ is a higher alkylcarbonyloxy radical have a long duration of action. Hence, the compounds of formula (I) only need to be administered at relatively large intervals, e.g. several days or weeks, the actual time of administration depending on the nature of the compound of formula (I) used and the condition of the subject to be treated. Consequently, the present compounds allow for a more efficient therapy: the slow elimination facilitates maintaining a stable plasma concentration at a non-toxic, effective level and the reduction in the number of administrations may be expected to result in better compliance of the subject to be treated with the prescribed medication.

In view of their useful pharmacological properties, the subject compounds may be formulated into various pharmaceutical forms for administration purposes. To prepare the pharmaceutical compositions of this invention, an effective amount of the particular compound, in acid addition salt or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) wherein $R^3$ is $R^4$—C(=O)—O— may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of diseases associated with the release of neurotransmitters, in particular in the treatment of psychotic diseases, it is evident that the present invention provides a method of treating warm-blooded animals suffering from such diseases, in particular psychotic diseases, said method comprising the systemic administration of an antipsychotic amount of a compound of formula (I) or a pharmaceutically acceptable acid addition salt thereof, effective in treating diseases associated with the release of neurotransmitters, in particular psychotic diseases. Those of skill in the treatment of such diseases could easily determine the effective amount from the test results presented hereinafter. In general it is contemplated that an effective antipsychotic amount would be from about 0.01 mg/kg to about 4 mg/kg body weight, more preferably from about 0.04 mg/kg to about 2 mg/kg body weight.

The following examples are intended to illustrate and not to limit the scope of the present invention. Unless otherwise stated all parts therein are by weight.

EXPERIMENTAL PART
A. Preparation of Intermediates

EXAMPLE 1 a) To a stirred mixture of 84 parts of phosphoryl chloride and 540 parts of methylbenzene were added 20 parts of 3-(phenylmethoxy)-2-pyridinamine. The mixture was stirred at 50° C. and 22 parts of 3-acetyl-4,5-dihydro-2(3H)-furanone were added. The reaction mixture was stirred for 5 hours at 90° C. Another portion of 22 parts of 3-acetyl-4,5-dihydro-2(3H)-furanone was added and stirring was continued for 30 minutes at 90° C. The solution was allowed to stand overnight at 90° C. The whole was poured into crushed ice and treated with an ammonium hydroxide solution 25%. The product was extracted with trichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was stirred in 2-propanol. The product was filtered off, washed with a mixture of 2-propanol and 1,1'-oxybisethane and dried at 50° C., yielding 20.5 parts (62.3%) of 3-(2-chloroethyl)-2-methyl-9-(phenylmethoxy)-4H-pyrido[1,2-a]pyrimidin-4-one; mp. 141.1° C. (intermediate 1) b) A mixture of 3.3 parts of 3-(2-chloroethyl)-2-methyl-9-(phenylmethoxy)-4H-pyrido[1,2-a]pyrimidin-4-one and 120 parts of methanol was hydrogenated at normal pressure and at room temperature with 2.0 parts of palladium-on-charcoal catalyst 10%. After the calculated amount of hydrogen was taken up, the catalyst was filtered off and the filtrate was evaporated to dry, yielding 2.4 parts (99%) of 3-(2-chloroethyl)-6,7,8,9-tetrahydro-9-hydroxy-2-methyl-4H-pyrido[1,2-a]pyrimidin-4-one as an oily residue. (intermediate 2)

EXAMPLE 2 a) A mixture of 17 parts of 5-methoxy-2-pyridinamine, 61 parts of phosphoryl chloride and 348 parts of methylbenzene was stirred for 2 hours at 60° C. 18 Parts of 3-acetyl-4,5-dihydro-2(3H)-furanone were added and the reaction mixture was stirred overnight at 90° C. The whole was poured into crushed ice and treated with ammonium hydroxide. The product was extracted with trichloromethane. The extract was dried, filtered and evaporated. The residue was stirred in a mixture of hexane and ethyl acetate (50:50 by volume). The precipitated product was filtered off and dried, yielding 10 parts (30.4%) of 3-(2-chloroethyl)-7-methoxy-2-methyl-4H-pyrido-[1,2-a]pyrimidin-4-one; mp. 150° C. (intermediate 3)

b) A mixture of 10 parts of 3-(2-chloroethyl)-7-methoxy-2-methyl-4H-pyrido[1,2-a]pyrimidin-4-one, 40 parts of 2-propanol saturated with hydrogen chloride and 160 parts of methanol was hydrogenated at normal pressure and at room temperature with 2.0 parts of palladium-on-charcoal catalyst 10%. After the calculated amount of hydrogen was taken up, the catalyst was filtered off over diatomaceous earth and the filtrate was evaporated. The oily residue was taken up in 80 parts of 2-propanol and 2,2'-oxybispropane. After stirring overnight at room temperature, the precipitated product was filtered off, washed with a mixture of 2-propanol and 2,2'-oxybispropane and dried in vacuo at 50° C., yielding 7.5 parts (64.0%) of 3-(2-chloroethyl)-6,7,8,9-tetrahydro-7-methoxy-2-methyl4H-pyrido[1,2-a]pyrimidin-4-one monohydrochloride; mp. 170° C. (intermediate 4)

c) A mixture of 6 parts of 3-(2-chloroethyl)-6,7,8,9-tetrahydro-7-methoxy-2-methyl-4H-pyrido[1,2-a]pyrimidin-4-one, 4.8 parts of 6-fluoro-3-(4-piperidinyl)-1,2-benzisoxazole monohydrochloride, 6.1 parts of N-(1-methylethyl)-2-propanamine and 16 parts of methanol was stirred overnight at reflux temperature. The reaction mixture was evaporated and the residue was taken up in water. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated, yielding 8.5 parts (100%) of 3-[2-[4-(6-fluoro-1,2-benzisoxazol-3-yl)-1-piperidinyl]ethyl]-6,7,8,9-tetrahydro-7-methoxy-2-methyl-4H-pyrido[1,2-a]-pyrimidin-4-one as an oily residue. (intermediate 5)

B. Final Compounds

EXAMPLE 3

A mixture of 12.5 parts of 3-(2-chloroethyl)-6,7,8,9-tetrahydro-9-hydroxy-4H-pyrido[1,2-a]pyrimidin-4-one, 10.0 parts of 6-fluoro-3-(4-piperidinyl)-1,2-benzisoxazole monohydrochloride, 10 parts of N-(1-methylethyl)-2-propanamine and 120 parts of methanol was stirred overnight at 60° C. The reaction mixture was evaporated and the oily residue was taken up in trichloromethane and washed with water. The organic layer was dried, filtered and evaporated. The residue was purified twice by column chromatography over silica gel first using a mixture of trichloromethane and methanol (95:5 by volume) and then a mixture of trichloromethane and methanol, saturated with ammonia (95:5 by volume) as eluents. The pure fractions were collected and the eluent was evaporated. The residue was crystallized from 2-propanone. After cooling, the precipitated product was filtered off, washed with a mixture of 2-propanol and 2,2'-oxybispropane and recrystallized from 2-propanol. The product was filtered off and dried, yielding 3.6 parts (21.1%) of 3-[2-[4-(6-fluoro-1,2-benzisoxazol-3-yl)-1-piperidinyl]ethyl]-6,7,8,9-tetrahydro-9-hydroxy-2-methyl-4N-pyrido[1,2-a]pyrimidin-4-one; mp. 179.8° C. (Compound 1)

EXAMPLE 4

To a stirred solution of 5.4 parts of 3-[2-[4-(6-fluoro-1,2-benzisoxazol-3-yl)-1-piperidinyl]ethyl]-6,7,8,9-tetrahydro-9-hydroxy-2-methyl-4N-pyrido[1,2-a]pyrimidin-4-one and 1.6 parts of NN-dimethyl-4-pyridinamine in 39 parts of dichloromethane was added dropwise a solution of 5.4 parts of (+)-3,4-dihydro-1N-2-benzopyran-2-carbonyl chloride in 39 parts of dichloromethane. Upon complete addition, stirring was continued for 4 hours at room temperature. The reaction mixture was washed successively with water, a sodium hydroxide solution 1N and water, dried, filtered and evaporated. The residue was purified by column chromatography over silica gel using a mixture of acetonitrile and water, saturated with ammonia (50:50 by volume) as eluent. Two pure fractions were collected and the eluent was evaporated. Each residue was salted out with sodium chloride and two diastereoisomeric esters were obtained. The first isomer was combined with 16 parts of methanol, 1 part of N-(1-methylethyl)2-propanamine and 1 part of water and the whole was stirred for 160 minutes at 60° C. The mixture was evaporated and the residue was purified by column chromatography over silica gel using a mixture of trichloromethane and methanol (90:10 by volume) as eluent. The pure fractions were collected and the eluent was evaporated. The residue was crystallized from 2-propanol. The product was filtered off and dried, yielding 0.2 parts (3.6%) of (+)-3-[2-[4-(6-fluoro-1,2-benzisoxazol-3-yl)-1-piperidinyl]ethyl]-6, 7,8,9-tetrahydro-9-hydroxy-2-methyl-4N-pyrido[1,2-a]-pyrimidin-4-one; mp. 160.7° C., $[\alpha]^D$=+15.42° (c=0.5% in ethanol). (Compound 2) The second isomer was combined with 16 parts of methanol, 1 part of N-(1-methylethyl)-2-propanamine and 1 part of water and the whole was stirred for 160 minutes at 60° C. The mixture was evaporated and the residue was purified by column chromatography over silica gel using a mixture of trichloromethane and methanol (90:10 by volume) as eluent. The pure fractions were collected and the eluent was evaporated. The residue was crystallized from 2-propanol. The product was filtered off and dried, yielding 0.2 parts (3.6%) of (−)-3-[2-[4-(6-fluoro-1,2-benzisoxazol-3-yl)-1-piperidinyl]ethyl]-6,7,8,9-tetrahydro-9-hydroxy-2-methyl-4N-pyrido[1,2-a]-pyrimidin-4-one; mp. 156.9° C., $[\alpha]^D$=−22.81° (c=0.5% in ethanol). (Compound 3)

EXAMPLE 5

A mixture of 4.3 parts of 3-[2-[4-(6-fluoro-1,2-benzisoxazol-3-yl)-1-piperidinyl]-ethyl]-6,7,8,9-tetrahydro-9-hydroxy-2-methyl-4H-pyrido[1,2-a]pyrimidin-4-one and 30 parts of acetic acid anhydride was stirred for 4 hours at 50° C. After cooling, the reaction mixture was poured into water and treated with an ammonium hydroxide solution. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated in vacuo. The residue was crystallized from 2,2'-oxybispropane. The product was filtered off and dried, yielding 3.0 parts (64.0%) of 3-[2-[4-(6-fluoro-1,2-benzisoxazol-3-yl)-1-piperidinyl]ethyl]-6,7,8,9-tetrahydro-2-methyl-4-oxo-4N-pyrido[1,2-a]pyrimidin-9-ol acetate (ester); mp. 143.6° C. (Compound 4) In a similar manner and by using butanoic acid anhydride as acylating reagent there was also prepared [3-[2-[4-(6-fluoro-1,2-benzisoxazol-3-yl)-1-piperidinyl]ethyl]-6,7,8,9-tetrahydro-2-methyl-4-oxo-4N-pyrido[1,2-a]pyrimidin-9-yl]butanoate, mp. 112.9° C. (Compound 5).

EXAMPLE 6

To a stirred solution of 1.2 parts of 3-[2-[4-(6-fluoro-1,2-benzisoxazol-3-yl)-1-piperidinyl]ethyl]-6,7,8,9-tetrahydro-9-hydroxy-2-methyl-4N-pyrido[1,2-a]pyrimidin-4-one in 21 parts of dichloromethane and 5 parts of water were simultaneously added dropwise a solution of 1.1 parts of decanoyl chloride in 13 parts of dichloromethane and a solution of 1 part of sodium hydroxide in 6 parts of water. Upon complete addition, stirring was continued for 2 hours at room temperature. Another portion of 1.1 parts of decanoyl chloride was added and stirring was continued overnight at room temperature. The product was extracted with dichloromethane. The extract was washed with water, dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in 2-propanol. The product was filtered off and dried, yielding 0.9 parts (45.9%) of [3-[2-[4-(6-fluoro-1,2-benzisoxazol-3-yl)-1-piperidinyl]ethyl]-6,7,8,9-tetrahydro-2-methyl-4-oxo-4-N-pyrido[1,2-a]pyrimidin-9-yl]decanoate dihydrochloride; mp. 221.4° C. (Compound 6)

EXAMPLE 7

A mixture of 8.5 parts of 3-[2-[4-(6-fluoro-1,2-benzisoxazol-3-yl)-1-piperidinyl]-ethyl]-6,7,8,9-tetrahydro-7-methoxy-2-methyl-4N-pyrido[1,2-a]pyrimidin-4-one, 14 parts of iodotrimethylsilane and 40 parts of acetonitrile was stirred overnight at 70° C. Another portion of 2.8 parts of iodotrimethylsilane was added and the reaction mixture was stirred for a while at 90° C. and then overnight at reflux temperature. After cooling, the whole was evaporated. The residue was taken up in ethanol and the whole was evaporated again. The residue was taken up in water and treated with a sodium hydroxide solution. The product was extracted with trichloromethane. The extract was dried, filtered and evaporated. The residue was purified by column chromatography over silica gel using a mixture of trichloromethane and methanol (95:5 by volume) as eluent. The desired fraction was collected and the eluent was evaporated. The residue was solidified in ethanol. The product was filtered off and dried, yielding 0.3 parts (3.7%) of 3-[2-[4-(6-fluoro-1,2-benzisoxazol-3-yl)-1-piperidinyl]ethyl]-6,7,8,9-tetrahydro-7-hydroxy-2-methyl-4N-pyrido[1,2-a]-pyrimidin-4-one; mp. 156.2° C. (Compound 7)

Following the procedure of example 6, compound 7 was converted to [3-[2-[4-(6-fluoro-1,2-benzisoxazol-3-yl)-1-piperidinyl]ethyl]-6,7,8,9-tetrahydro-2-methyl-4-oxo-4N-pyrido[1,2-a]-pyrimidin-7-yl] decanoate. (Compound 8)

C. Pharmacological Examples

EXAMPLE 8

The antipsychotic activity of the subject compounds is evidenced by the experimental data obtained in at least one of two different test procedures, viz. the combined apomorphine (APO), tryptamine (TRY) and norepinephrine (NOR) test in rats, and the apomorphine test in dogs. Said combined apomorphine, tryptamine and norepinephrine test is described in Ach. int. Pharmacodyn., 227, 238–253 (1977) and provides an empirical evaluation of the relative specificity with which drugs may effect particular neurotransmitter systems centrally (CNS) as well as peripherally. In particular, the test demonstrates the antagonistic activity of the tested compounds of formula (I) on dopamine (by preventing the symptoms elicited with the dopamine agonist apomorphine), on serotonin (by preventing the central and peripheral symptoms (convulsions; hyperaemia) elicited with serotonin or tryptamine), and on norepinephrine (by preventing or delaying death upon administration of the $\alpha_2$-agonist norepinephrine). Said pomorphine test in dogs is described in Arzneim.-Forsch. (Drug Res.), 9, 765–767 (1959) and provides a measure of the duration of action of the tested compounds. The tests are carried out following the procedures described in EP-A-0,196,132 and the experimental data are summarized in Table 1.

TABLE 1

| | Combined test in rats; $ED_{50}$ in mg/kg | | | | (APO)-dog test, $ED_{50}$ in mg/kg | | |
|---|---|---|---|---|---|---|---|
| Comp No. | (APO) | (TRY)-convulsions | (TRY)-hyperaemia | (NOR) | 1 hr | 4 hr | 16 hr |
| 1 | 0.25 | 0.31 | 0.002 | 0.08 | 0.015 | 0.015 | 0.015 |
| 2 | 0.31 | 0.08 | 0.00031 | 1.25 | 0.015 | 0.03 | 0.06 |
| 3 | 0.31 | 0.31 | 0.00063 | 0.63 | 0.008 | 0.007 | 0.015 |
| 4 | 0.31 | 0.08 | 0.00031 | 0.31 | 0.015 | * | * |
| 5 | 0.31 | 0.31 | 0.00125 | 0.16 | 0.008 | * | * |

*: not tested.

D. Composition Examples

EXAMPLE 9

Oral Drops

500 Parts of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 10

Oral Solution

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 11

Capsules

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, comprising each 20 mg of the active ingredient.

EXAMPLE 12

Film-Coated Tablets
Preparation of Tablet Core
A mixture of 100 parts of the A.I., 570 parts lactose and 200 parts starch was mixed well and thereafter humidified with a solution of 5 parts sodium dodecyl sulfate and 10 parts polyvinylpyrrolidone (Kollidon-K 90®) in about 200 ml of water. The wet powder mixture was sieved, dried and sieved again. Then there was added 100 parts microcrystalline cellulose (Avicel®) and 15 parts hydrogenated vegetable oil (Sterotex®). The whole was mixed well and compressed into tablets, giving 10.000 tablets, each containing 10 mg of the active ingredient.

Coating

To a solution of 10 parts methyl cellulose (Methocel 60 HG®) in 75 ml of denaturated ethanol there was added a solution of 5 parts of ethyl cellulose (Ethocel 22 cps®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 13

Injectable Solution 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 14

Suppositories

3 Parts A.I. was dissolved in a solution of 3 parts 2,3-dihydroxybutanedioic acid in 25 ml polyethylene glycol 400. 12 Parts surfactant (SPAN®) and triglycerides (Witepsol 555®) q.s. ad 300 parts were molten together. The latter mixture was mixed well with the former solution. The thus obtained mixture was poured into moulds at a temperature of 37–38° C. to form 100 suppositories each containing 30 mg/ml of the A.I.

EXAMPLE 15

Injectable Solution

60 Parts of A.I. and 12 parts of benzylalcohol were mixed well and sesame oil was added q.s. ad 1 l, giving a solution comprising 60 mg/ml of A.I. The solution was sterilized and filled in sterile containers.

What is claimed is:
1. A process for preparing an enantiomeric form of the compound having the formula:

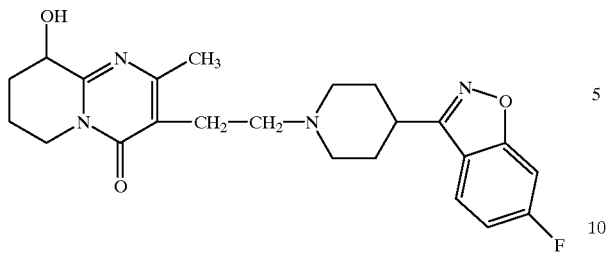

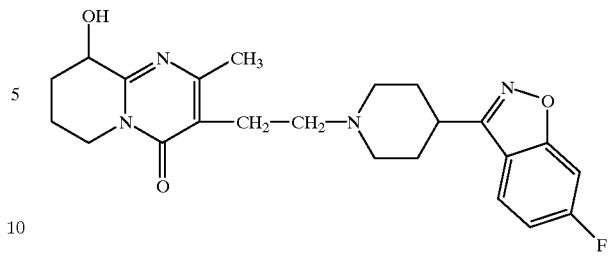

or a pharmaceutically acceptable acid addition salt thereof, wherein said process comprises the steps of:

(a) reacting a racemic mixture of said compound with chiral 4,5-dihydro-1H-2-benzopyran-2-carboxylic acid or the acid chloride thereof, to form a mixture of diastereomeric esters;

(b) physically separating said mixture of diastereomeric esters by chromatography; and (c) converting said separated diastereomeric salts or esters into the corresponding enantiomeric forms of said compound by hydrolysis in an acidic or basic aqueous medium.

2. The process of claim 1 wherein the enantiomeric form of said compound recovered is (+)-3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one.

3. The process of claim 1 wherein the enantiomeric form of said compound recovered is (−)-3-[2-[4-(6-fluoro-1,2-benzisoxazol-3-yl)-1-piperidinyl]ethyl]-6,7,8,9-tetrahydro-9-hydroxy-2-methyl-4H-pyrido [1,2-a]pyrimidin-4-one.

4. A process for preparing an enantiomeric form of the compound having the formula:

or a pharmaceutically acceptable acid addition salt thereof, wherein said process comprises the steps of:

(a) reacting a racemic mixture of said compound with a chiral acid or acid chloride selected from the group consisting of tartaric acid, malic acid, mandelic acid, camphor sulfonic acid, 4,5-dihydro-1H-2-benzopyran-2-carboxylic acid, and the acid chlorides thereof, to form a mixture of diastereomeric salts or esters;

(b) physically separating said mixture of diastereomeric salts or esters by selective crystallization or chromatography; and (c) converting said separated diastereomeric salts or esters into the corresponding enantiomeric forms of said compound by hydrolysis in an acidic or basic aqueous medium.

5. The process of claim 4 wherein the enantiomeric form of said compound recovered is (+)-3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one.

6. The process of claim 4 wherein the enantiomeric form of said compound recovered is (−)-3-[2-[4-(6-fluoro-1,2-benzisoxazol-3-yl)-1-piperidinyl]ethyl]-6,7,8,9-tetrahydro-9-hydroxy-2-methyl-4H-pyrido [1,2-a]pyrimidin-4-one.

* * * * *